United States Patent [19]

McClure

[11] 4,374,090
[45] Feb. 15, 1983

[54] CHEMICAL BIAS AGENT DETECTION

[75] Inventor: B. Thompson McClure, Hopkins, Minn.

[73] Assignee: Honeywell Inc., Minneapolis, Minn.

[21] Appl. No.: 280,438

[22] Filed: Jul. 6, 1981

[51] Int. Cl.³ .................. G01N 27/66; G01N 27/70
[52] U.S. Cl. ............................ 422/98; 324/469; 324/464; 250/308; 250/432 R
[58] Field of Search .................. 422/94–98, 422/54; 73/861.09; 250/308, 435, 436, 437, 432 R; 324/469, 464

[56] References Cited

U.S. PATENT DOCUMENTS

| | | | |
|---|---|---|---|
| 3,540,851 | 11/1970 | Vree et al. | 422/98 |
| 3,835,328 | 9/1974 | Harris et al. | 250/308 |
| 4,075,550 | 2/1978 | Castleman et al. | 250/308 |
| 4,148,612 | 4/1979 | Taylor et al. | 422/98 |
| 4,150,951 | 4/1979 | Capelle et al. | 422/98 |
| 4,203,726 | 5/1980 | Patterson | 422/54 |
| 4,309,187 | 1/1982 | Dodge et al. | 422/98 |

*Primary Examiner*—Michael S. Marcus
*Attorney, Agent, or Firm*—Omund R. Dahle

[57] ABSTRACT

The present invention is directed to an ionization cell for detecting the presence of very minute concentrations of certain chemical agents. The effective sensitivity of conventional chemical agent detectors is restricted in the presence of certain interferants such as jet fuel, gasoline, smoke, turpentine and the like. Herein a "chemical bias," that is a background concentration of a simulant is provided at the inlet of an ionization detector, which chemical bias is effective by charge exchange to prevent the interferants from dominating the signal.

5 Claims, 5 Drawing Figures

CHEMICAL BIAS AGENT DETECTION

BACKGROUND AND SUMMARY OF THE INVENTION

The present invention relates to chemical agent detection by ionization cells of the type generally described in U.S. Pat. No. 3,835,328. Such cells can be used to detect the presence of very minute concentrations of a select group of chemical vapors or gases in the air or in other vapor or gas backgrounds. Described in U.S. Pat. No. 3,835,328 is an ionization-type detector in which a gas sample flows past a source of ionization and through an attrition region to an ion collection region. A collector current is produced as a function of the concentration of positive ions and the concentration of negative ions in the gas sample reaching the collector region; the electrical potential of the collector and the rate of gas flow. By "attrition" in this invention is meant recombination in the flowing gas as well as removal from the gas to the walls by diffusions and turbulent transport.

By providing a long path and an exposure to adequate surface, the attrition of ions is enhanced and controlled in such a way that ion concentration, and in particular the difference between the concentration of positive ions and negative ions remaining in the gas sample when it reaches the collection region, is a function of trace gases in the sample. An improved gas ionization cell with compensation for variations in the flow rate of the gas and variations in radioactive source intensity is shown in U.S. Pat. No. 4,075,550 issued to Castleman et al and assigned to the same assignee as the present invention. This is accomplished by taking a portion of the gas sample, after it has been exposed to the ionizing radiation, and directing this portion of the gas sample past a pair of flow probes through a channel which bypasses the attrition region of the cell. The signal generated at the flow probes is proportional to the gas flow rate and the ionizing source intensity and is combined with the signal at the collector screen which is a function of the trace gas. A limitation is that although the prior art is capable of responding to the required low concentration, its use at high sensitivity settings is restricted because it also has a response to interferants. "Interferants" denotes any of a class of substances which causes an undesired signal, that is, a chemical noise. The response of such sensor cells as described above depends on two effects: the vapors in the air must form ions and the ions must survive transport through the cell.

In the present invention a "chemical bias," that is, a background concentration of a simulant, is provided to the inlet of an ionization detector of the general type shown in the references above and that is effective, by charge exchange, to prevent large concentrations of materials (interferants) such as jet fuel, gasoline, smoke, turpentine and the like from dominating the signal. The introduction of this chemical bias at the inlet suppresses the response of high concentrations of interference materials and thereby increases the useful "signal-to-noise" ratio of the chemical agent detectors.

DESCRIPTION

Figure 1:
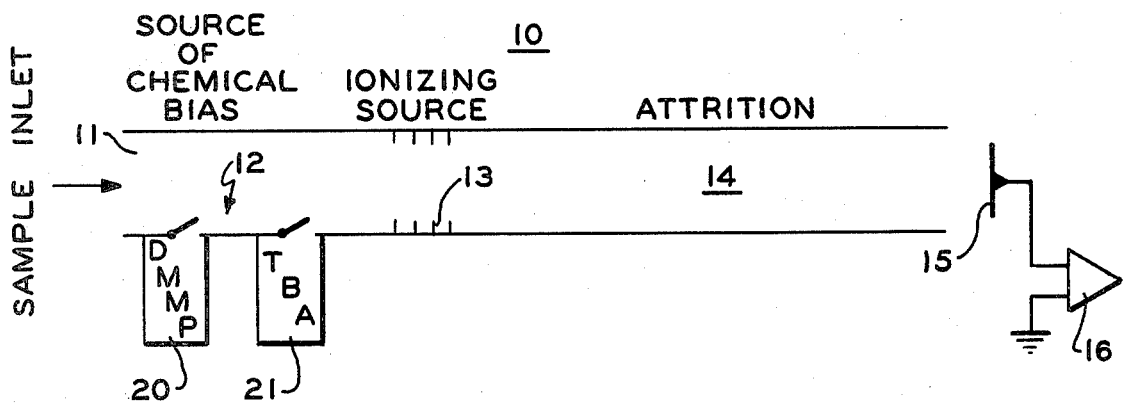
FIG. 1 is a schematic representation of the apparatus according to the invention.

Referring now to FIG. 1 there is disclosed a chemical agent detector in the form of an ionization cell 10 in which a gas sample enters at a sample inlet 11 and flows past a source of chemical bias 12, a source of ionization 13 and through a region 14 in which attrition of the ions occurs by recombination directly in the gas or by diffusion to the surrounding surfaces and then to an ion collector region 15. The ionization source 13 may be a source of radioactivity, a corona or other source which ionizes the gas sample. A resulting electrical signal at the ion collector is of a magnitude which is a function of the ion concentration and the proportion of positive vs. negative ions in the gas sample after passing through the attrition region 14. The ion collector 15 is electrically connected to suitable amplifying means 16. The response of the sensor depends on both vapors in the air which form ions, and then that the ions must survive transport through the cell. Sensors of this type have had a limitation in that certain common interferants such as jet fuel, gasoline, turpentine, smoke and perhaps others contain many substances which form ions and give a significant signal.

The present invention is directed to introducing a bias chemical into the entering air stream prior to the ionization. The bias chemical forms ions which are characterized by smaller ionization energies than those formed by the common interferants but larger than those formed by the agents to be detected. Consequently, interferant ions are converted to bias ions by charge exchange. In this invention the addition of a source of chemical bias 12 to the system is the novel improvement. In this embodiment the source of chemical bias 12 is shown as two canisters or permeation tubes 20 and 21 containing the selected chemical bias materials. The canisters can be selectively or simultaneously opened to the flow path of the sample gas. The provision of more than one bias material allows for the achieving of some added selectivity in the operation of the invention. As an example the canisters are indicated as containing DMMP (dimethylmethyl phosphonate) in one and TBA (tributylamine) in the other. Other chemical bias materials such as DIMP (diisopropylmethyl phosphonate), di-N-butylamine or DMSO (dimethylsulfoxide), for example, may be selected.

In this invention the chemical bias, such as DMMP is continually introduced at the sample inlet from bias source 20. This bias forms molecular ions that are heavier and have smaller ionization energy than the interference materials but are lighter and have higher ionization energy than the true agents to be detected.

Said another way, the desired bias chemical for this invention has an ionization potential and diffusion coefficient less than those of common interferants but greater than those of the real agents. This allows the recognition of a small concentration of agent in the presence of a large concentration of interferants. The background concentration of bias chemical (simulant) prevents, by charge exchange, large concentrations of interferants such as jet fuel, turpentine or smoke from dominating the signal. The present understanding of the invention is that true agent ions have a signature which includes lower ionization potential and higher molecular weight than some bias materials so that the agents do induce a signal in the presence of a bias. Although the source of chemical bias 20 has been described in FIG. 1 in the inlet flow path prior to the ionizing source 13, it need not necessarily be prior to the ionizing source and the bias may alternately be introduced at the same location as the ionization source.

In addition the agent to be detected must also have a favorable reaction rate for charge exchange with the bias chemical so that adequate sensitivity is obtained. The effect on the cell response is as follows. When drawing in clean filtered air the cell would generate a constant signal due to the bias chemical which would be somewhat higher in magnitude than present cell responses to filtered air. When a contaminant is present, it would have to compete with the bias chemical for the available ions and the ultimate cell response would ideally either remain nearly the same or even decrease somewhat. When agent is present, it forms ions more efficiently than the bias chemical, the ions would be heavier, and thus cell response would increase. Agent signal-to-interference signal is improved and thereby allows operating the current cell with a higher gain thus increasing the sensitivity to agents.

Figure 2:
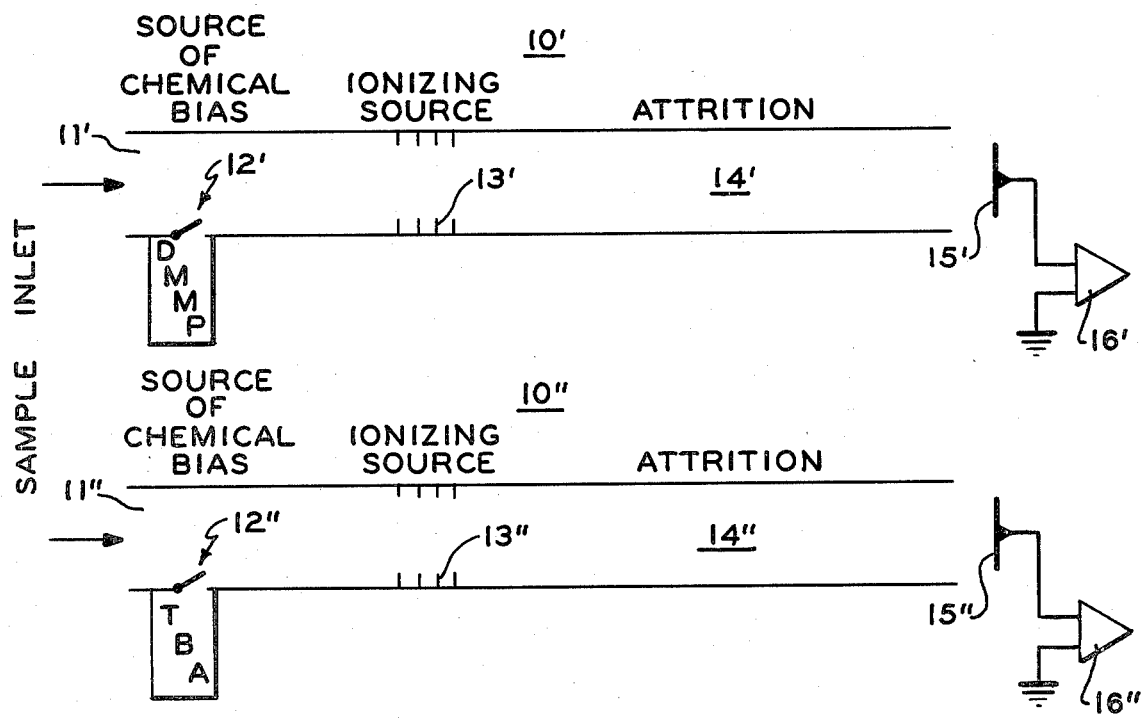
FIG. 2 is a schematic representation of another embodiment of the invention.

Another embodiment of the invention is shown in FIG. 2. This figure is basically similar to that previously described however it has two parallel channels 10' and 10''. Also only one bias agent canister is associated with each channel.

Figure 3:
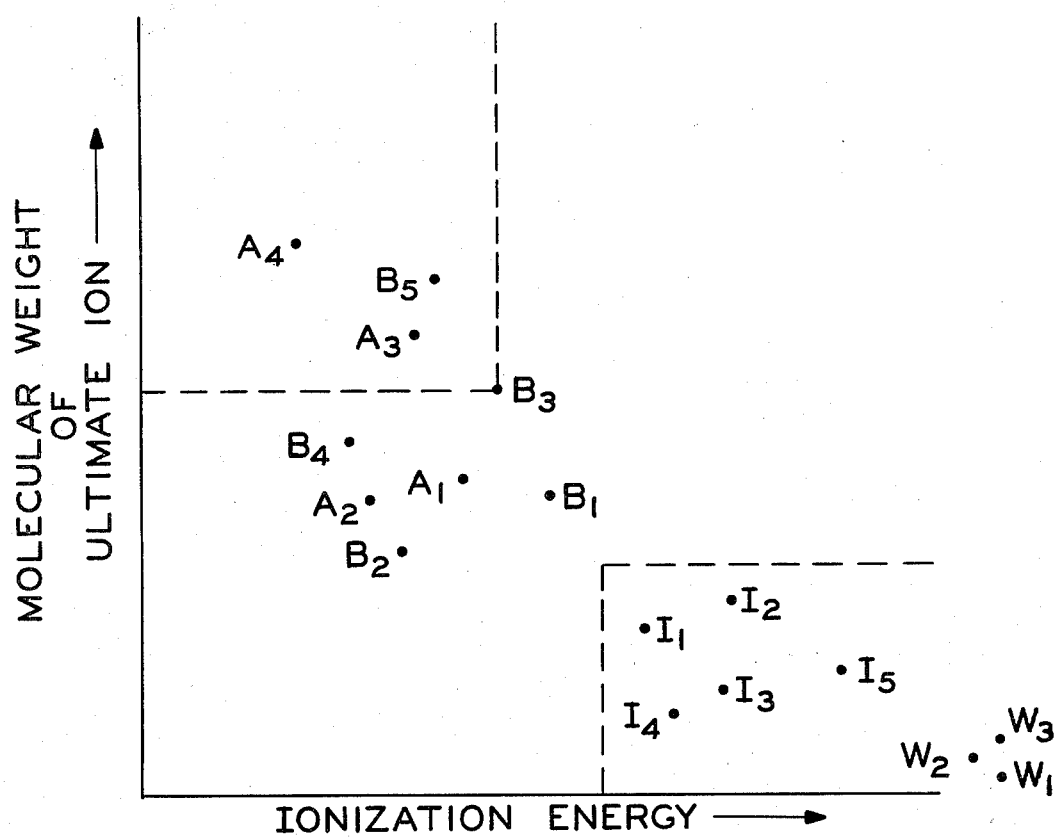
FIG. 3 is a graphical presentation of the effective molecular weight of the ultimate species of ions produced in the presence of various interferants, bias chemicals and agents ions versus ionization energy for applications in which the agent to be detected is characterized by producing ions of unusually low ionization energy.

Referring now to FIG. 3 there is shown schematically the interrelationship between various interferants (I); bias chemicals (B); natural ions in clean air (W); and agents (A), on a graph which has on the ordinate axis "molecular weight of ultimate ion" and on the absissa has "ionization energy". The sequence (re-ionization energy) in this graph is related to the proclivity of material for charge-exchange with those of higher energy. As to the effective molecular weight of the ultimate species of ion produced in the presence of various interferants, bias chemicals and agents ions, there is a direct relationship to the response of ionization type detectors and an inverse relation to diffusion and mobility. In FIG. 3 information about which agent ($A_1$, $A_2$, $A_3$, $A_4$) is present can be found from the results of a series of experiments with biases ($B_1$, $B_2$ etc.) For example with bias chemical $B_3$ present, a response to agents $A_3$ and $A_4$ only is expected. This is because the agents $A_3$ and $A_4$ have a lower ionization energy (potential) and a higher mass (molecular wt) than the bias chemical $B_3$. The agents $A_3$ and $A_4$ accomplish the charge exchange because they are to the left of bias $B_3$ (i.e., lower ionization energy) and provide a signal because they are higher than $B_3$ (i.e., they have a higher mass). Agents $A_1$ and $A_2$ do not provide a response in the presence of $B_3$ because although they are to the left (lower ionization energy), they are of lower mass than bias $B_3$.

Figure 4:
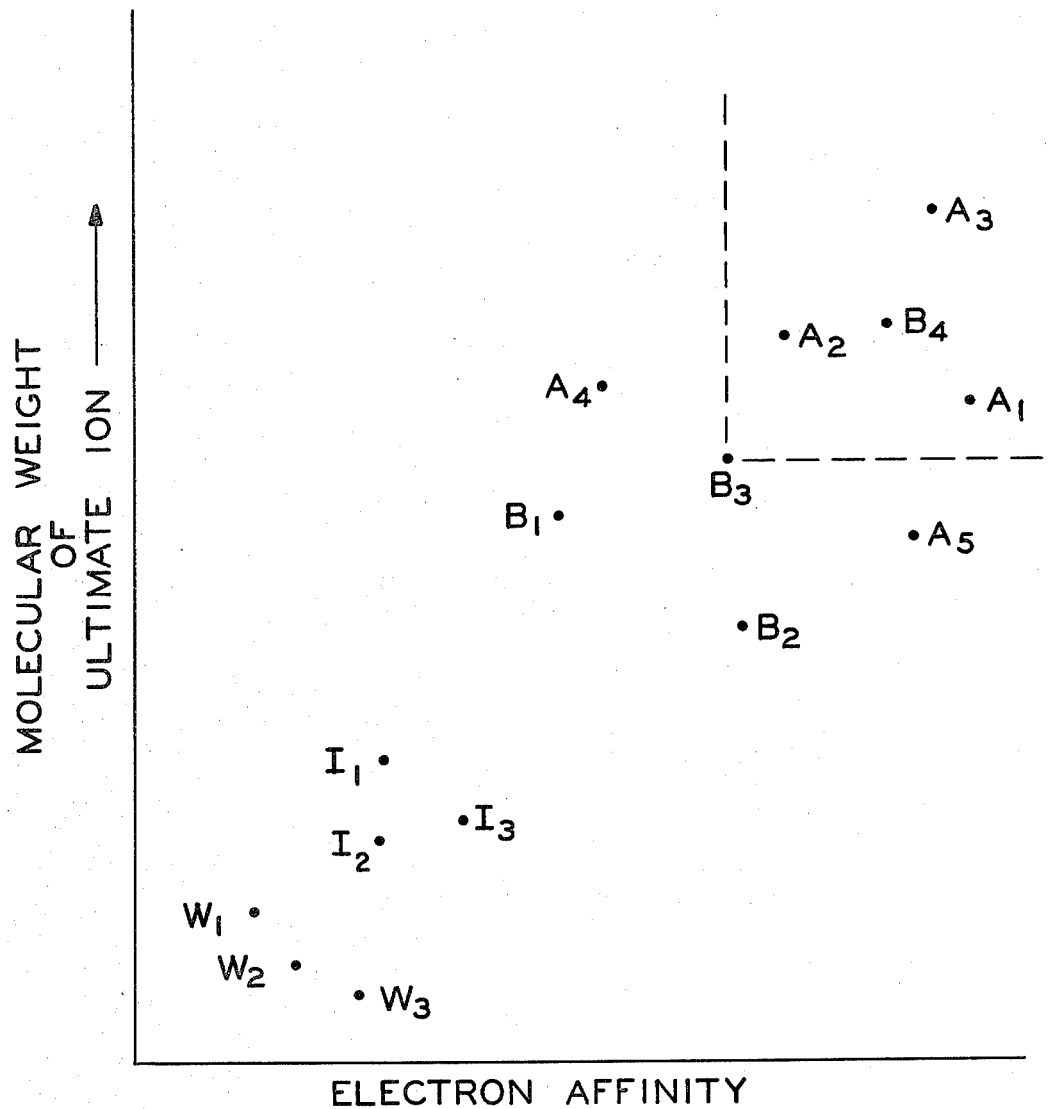
FIG. 4 is a graphical presentation of the effective molecular weight of the ultimate species of ions produced versus their electron affinity for applicatons in which the agent to be detected is characterized by an unusually large electron affinity.

FIG. 4 is a graphical presentation of the effective molecular weight of the ultimate species of ions produced versus their electron affinity for applications in which the agent to be detected is characterized by an unusually large electron affinity. As in the previous figure there is shown schematically the interrelationship between various interferants (I); bias chemicals (B); natural ions in clean air (W); and agents (A). The bias chemical has a lower electron affinity and a lower mass than the agent being detected.

Figure 5:
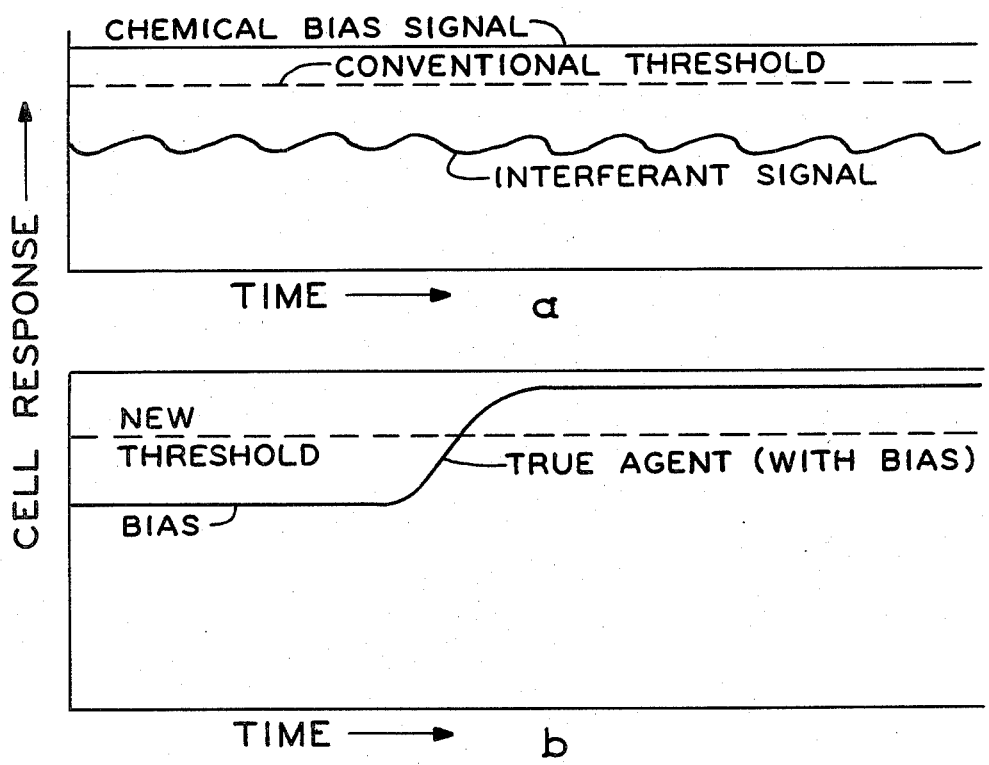
FIG. 5 is a graphical presentation of cell response versus time under several conditions.

FIG. 5 is a schematic plot of cell response versus time corresponding to various materials added to the carrier gas. At FIG. 5a it can be seen that the various interferants to which the cell responds can produce an interferant signal which in effect is a noise level nearly up to the conventional threshold as shown. In the present invention by the addition of the chemical bias which takes the charge from the interferants, there is added a chemical bias signal level which exceeds the conventional threshold at all times. Thus in FIG. 5b the chemical bias signal is reproduced again at the left of the graph with a new and higher threshold. When the true agent is sensed and this value is added to the chemical bias signal it may be seen that the solid line increases sharply to exceed the new threshold and thereby indicate the presence of the true agent.

The embodiments of the invention in which an exclusive property or right is claimed are defined as follows:

1. An ionization type chemical agent detector with a chemical bias comprising:

a housing having an inlet and an outlet for passage of gas samples;

means defining a source of a chemical bias agent selected from the group consisting of dimethylmethyl phosphonate, dissopropylmethyl phosphonate, di-N-butylamine, tributylamine and dimethyl sulfoxide connected to the housing to add said bias chemical to the incoming gas samples;

means defining a source of ionization mounted in the housing to ionize said incoming gas samples;

means defining an attrition region in said housing downstream from said source of ionization;

and a collector electrode mounted near said housing outlet for generating an electric signal which is a function of ions present in the gas sample after passing through said attrition region.

2. The detector according to claim 1 in which the bias chemical is dimethylmethyl phosphonate.

3. The detector according to claim 1 in which the bias chemical is tributylamine.

4. The detector according to claim 1 in which said bias chemical yields ultimate charged species (ions) which have higher ionization potentials and lower masses than the ultimate ion species which result when an agent to be detected is present and which bias chemical has a lower ionization potential and a higher mass than the interferants.

5. The detector according to claim 1 in which said bias chemical has a lower electron affinity and a lower mass than the agent being detected.

* * * * *